(12) United States Patent
Bourne

(10) Patent No.: US 10,238,784 B2
(45) Date of Patent: Mar. 26, 2019

(54) SYSTEM AND METHOD FOR PERITONEAL DIALYSIS

(71) Applicant: Newsol Technologies Inc., Caledon (CA)

(72) Inventor: Orson Bourne, Ottawa (CA)

(73) Assignee: Newsol Technologies Inc., Caledon (CA)

(*) Notice: Subject to any disclaimer, the term of this patent is extended or adjusted under 35 U.S.C. 154(b) by 0 days.

(21) Appl. No.: 15/537,187

(22) PCT Filed: Dec. 11, 2015

(86) PCT No.: PCT/CA2015/051312
§ 371 (c)(1),
(2) Date: Jun. 16, 2017

(87) PCT Pub. No.: WO2016/095026
PCT Pub. Date: Jun. 23, 2016

(65) Prior Publication Data
US 2017/0368249 A1    Dec. 28, 2017

Related U.S. Application Data

(60) Provisional application No. 62/092,894, filed on Dec. 17, 2014.

(51) Int. Cl.
*A61M 1/28* (2006.01)

(52) U.S. Cl.
CPC .............. *A61M 1/282* (2014.02); *A61M 1/28* (2013.01); *A61M 2205/127* (2013.01);
(Continued)

(58) Field of Classification Search
CPC .. A61M 1/282; A61M 1/28; A61M 2205/127; A61M 2205/3306;
(Continued)

(56) References Cited

U.S. PATENT DOCUMENTS 9,149,045 B2 * 10/2015 Lee .................. A01N 31/08
2002/0120227 A1    8/2002 Childers et al.
(Continued)

FOREIGN PATENT DOCUMENTS

| EP | 0157024 | 10/1985 |
| WO | WO2008086619 | 7/2008 |
| WO | WO2013185080 | 12/2013 |

*Primary Examiner* — Manuel A Mendez
(74) *Attorney, Agent, or Firm* — McMillan LLP

(57) ABSTRACT

The invention relates to a system of performing an evidence Dialysis modality of Batch, Tidal or a combination of both. The system: isolates cavity volume changes due only to ultrafiltrate; determines the volume of a patient cavity; determines a full cavity; determines an objective time to initiate an exchange; and determines an empty cavity. One or more combination of these features provide for evidence base Fill, Dwell, and Drain sequences. The system comprises: a cassette having a heated region and a sensor region for measurements. A valve manifold supplies a patient connection with fluid. A microprocessor receives pressure measurements, controls the heated region and activates a volumetric pump to deliver or extract discrete increments of the fluid to the cassette from bags. Filtering pressure measurements to remove rapid fluctuations determines an accumulated pressure in the patient cavity. The volume of fluid in the patient cavity correlates to the accumulated pressure.

35 Claims, 12 Drawing Sheets

(52) U.S. Cl.
CPC ............... *A61M 2205/3306* (2013.01); *A61M 2205/3344* (2013.01); *A61M 2205/3368* (2013.01)

(58) Field of Classification Search
CPC .. A61M 2205/3344; A61M 2205/3368; A61M 1/281; A61M 1/285; A61M 1/287; A61M 1/288; A61M 2205/502; B01D 61/32; B01D 61/30
USPC .......................................................... 604/29
See application file for complete search history.

(56) References Cited

U.S. PATENT DOCUMENTS

| | | |
|---|---|---|
| 2010/0137782 A1 | 6/2010 | Jaanson et al. |
| 2014/0018727 A1 | 1/2014 | Burbank et al. |

\* cited by examiner

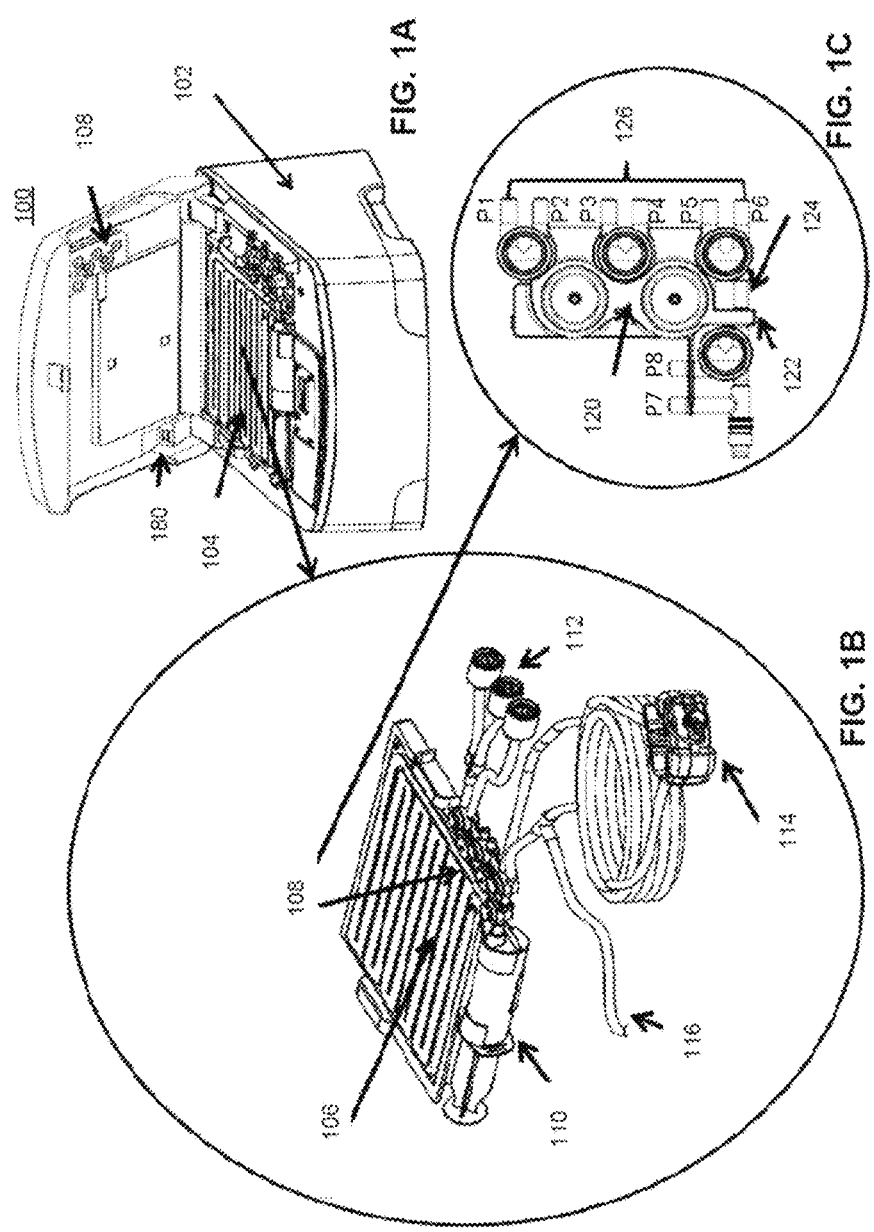

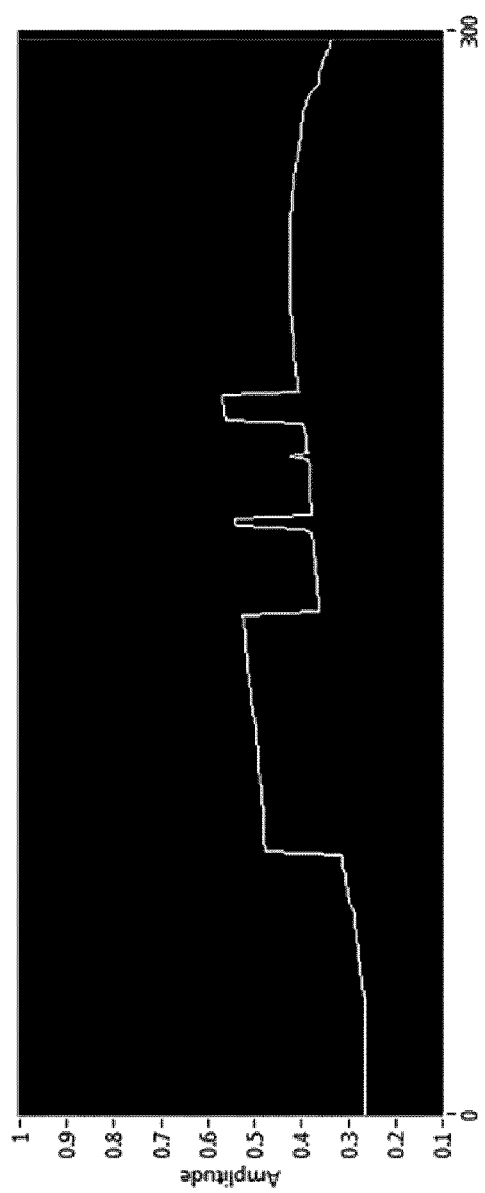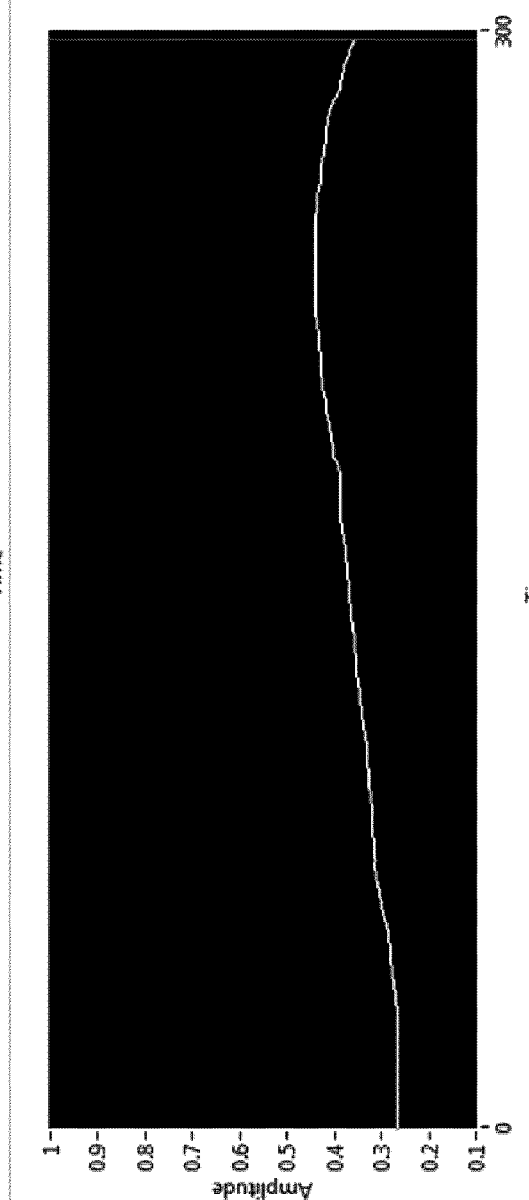

SYSTEM AND METHOD FOR PERITONEAL DIALYSIS

RELATED APPLICATIONS

This application claims priority from U.S. Provisional Patent Application No. 62/092,894, filed Dec. 17, 2014. The contents of which are incorporated by reference.

FIELD OF THE INVENTION

The present invention relates generally to dialysis systems and methods. More particularly, it relates to an improved peritoneal dialysis (PD) system, apparatus and methods for use therewith.

BACKGROUND OF THE INVENTION

For patients suffering from low kidney functions, dialysis is the standard treatment for replicating the function of a normal human kidney. There are two types of dialysis procedures in use, hemodialysis (HD), which circulates the patient's blood through filters located outside the body, and peritoneal dialysis (PD), which uses the peritoneal membrane of the patient's abdominal cavity as a filter to remove toxins via specialized solutions called dialysates.

Compared to HD, PD is a very gentle modality, with its slow corrective action more resembling that of the natural kidney. It is operationally simple, eliminates the need for venipunctures and has lower operational costs. Because the system is not an extracorporeal one, there is no need for a high degree of heparinization, a factor that is especially important in the case of diabetic patients. However, to date HD has continued to dominate in the treatment of End-Stage Renal Disease (ESRD) patients.

In a continuing effort to provide adequate PD treatment for the varied population of patients in need, clinicians have developed a number of different forms of PD modalities collectively known as the Automatic Peritoneal Dialysis (APD) modality. These include the APD modalities of: (i) Continuous Cycling Peritoneal Dialysis (CCPD); a method of performing PD in which an automated cycler performs 4 to 6 regular exchanges every night; (ii) Intermittent Peritoneal Dialysis (IPD); a method of performing PD in hospitals or at home with an automatic cycler two or three times a week for a period of about eight to twenty hours each time; (iii) Nightly Peritoneal Dialysis (NPD); a method of performing nightly peritoneal dialysis at home for patients with high efficiency peritoneal membranes. Such patients do not fare well with long dialysate dwell times.

These modalities all involve an infusion phase, during which the dialysate (normally glucose) is introduced into the peritoneal cavity (Fill), a Dwell phase during which the dialysate is essentially at rest in the peritoneal cavity, and a draining phase following the dwell phase, when the dialysate is expelled from the peritoneal cavity. The majority of the cleansing process takes place during the Dwell. It is this phase that removes the waste products, known as the Ultrafiltrate (UF), from the blood.

With currently available cyclers, there is no evidence-based method to determine when an individual Dwell phase within a treatment should be terminated. In such systems a fixed Dwell time is allocated for every given cycle. This time is adhered to regardless of the status of the UF conditions during that cycle. If the Dwell is allowed to proceed beyond the point when ultrafiltration has ceased, there is a danger of enhanced absorption of Glucose due to the reversal of the flow kinetics. Therefore, it is not uncommon to get glucose transported into the patient body using current cycler technology. This danger is significant during long Dwell periods. To combat this danger significantly more expensive osmotic agents, such as Icodextrine, are being used for long dwell periods. Alternatively, if the Dwell is terminated prematurely the patient does not receive the target dosage.

At least three other major limitations have been recognized with the standard Batch modalities. These are (a) a reduction in the quality of the dialysate during the long Dwell period due to its presence of the UF components; (b) longer than optimum Drain periods that limits the actual time available for the Dwell; and (c) the likelihood of Drain pain at the end of every cycle. This occurs when the cycler attempts to remove fluid from a cavity that is empty before the estimated total drain volume for that cycle has been achieved. This latter issue results from the fact that in the standard cycler, the drain volume is calculated based on an estimate of the expected UF for that cycle and not the actual UF generated during that cycle.

In an attempt to remove these limitations, the modality known as Tidal Peritoneal Dialysis (TPD) was developed. This modality utilizes an initial maximum dialysate fill volume (usually three liters) and periodically, during a long and continuous dwell time, drains a fraction of the infused volume (usually one-third, the tidal volume and known as the Tidal exchange volume) and re-infuses about a similar amount, adjusting for the UF into the patient. Since there may always be fluid present in the cavity, UF occurs during the Drain and subsequent Fill phases. This additional UF adds to that which occurred during the normal Dwell. The net effect is an increase of the effective "Dwell" time, a positive outcome since the Dwell is when the treatment is at its optimum. This methodology ensures that the quality of the dialysis is kept as high as practical within the limitation of the practiced art and that the effective treatment time (Dwell time) is maximized.

The waste transport mechanism that generates the UF is primarily driven by diffusion as a result of the osmotic gradient between the dialysate and the blood. Therefore the attributes of TPD should generate more UF clearance. Unfortunately to date there is no clear evidence that this is the case. See for example Alok Agrawal and Karl D. Nolph, *Advantages of Tidal Peritoneal Dialysis*, Peritoneal Dialysis International, May 2000, Vol. 20, Suppl. 2, herein incorporated by reference.

TPD consumes more dialysate than any of the other mentioned modalities therefore its cost is higher. The benefit of this additional cost is the potential to reduce pain events since the cavity is only completely emptied once during the treatment. In the other modalities the cavity is emptied multiple times in a treatment and due to the basic nature of prior Drain algorithms, multiple pain events have been recorded during a full treatment.

A number prior systems can perform TPD such as for example European Patent Application No. EP0498382 to Peabody. EP0498382 describes a device that can be used for TPD. The dialysate parameters do not vary and there is no evidence-based method to determine when to perform a Tidal exchange. The frequency and volume exchanged are constant, but the residual volume in the cavity increases over time. This increase in volume was not programmed but is due to the UF that is generated.

U.S. Pat. No. 8,585,634 B2 to Neftel reports a TPD methodology that suggest evidence based exchange times where a mathematical model predicts the times and volumes required. U.S. Patent Publication No. US2012/310056A refines on this model where the inputs rely on either the Personal Dialysis Capacity (PDC) test or the Peritoneal Equilibrium (PET) test. These tests provide transport kinetics of the peritoneum at the time of the test. However, the transport kinetics vary from day to day and cycle by cycle. Moreover the patient's diet and current clinical condition at the time of treatment also affects transport kinetics. Consequently, the numbers generated by such test are only the predicted or expected real time transport properties of the peritoneum at the time of a future treatment. In short they do not provide the actual transport kinetics parameters for real time evidence based determination of any of the exchange parameters. These include but are not limited to exchange volume, exchange time and exchange formulation.

It is common to inject a Last Fill at the end of the TPD cycle, which remains within the patient cavity until the next treatment. This is sometimes referred to as the WET volume. The previously mentioned systems lack the ability to determine if the cavity is truly empty at the final Drain. If the cavity is not empty at the end of the TPD cycle then the actual WET volume will be larger than prescribed resulting in patient discomfort. An example of this approach to TPD is given by U.S. Pat. No. 9,147,045. In this approach, a kinetic model is used to generate a series of UF curves from a limited set of discrete data points collected over a number of separate Dwell periods. The model is used to extrapolate between the discrete data points. The method then selects five individual prescriptions from a suite of possible prescriptions that can generate these curves in accordance to the kinetic model. This method assumes that these five prescriptions meet the individual needs of all patients, which may not be the case since no two patients present identical clinical conditions. The method also assumes that the prescription range is large enough to accommodate any variances that could occur on a daily basis. Furthermore, once the prescription has been initiated no changes can be made during the actual treatment. This method, like in U.S. Publication No. 2012/310056, cannot determine when the cavity is truly empty. Therefore, a high probability exists that the UF is under-estimated and consequently at the next Last Fill the actual volume in the cavity is higher than what is programmed. This combination leads to the clinically dangerous "overfill condition" for the patient.

U.S. Pat. No. 6,228,047 to Dadson and assigned to Newsol Technologies, Inc., assignee of the present application, the contents of which are herein incorporated by reference, discloses a method to address the overfill condition by monitoring the cavity pressure and a method to track and determine the rate of UF production. From these combined methods, it may be possible to arrive at an optimum exchange time if the disclosed methodologies is applied to the Tidal process. However, Dadson assumes that the only pressure rise is due to UF production. This is not the case. For example, patient movement during the night can generate abrupt and large swings in pressure. Also, normal biological functions are superimposed on any observable pressure changes. The method proposed by Dadson gradually reduces the volume of dialysate in the cavity during the Dwell each time the pressure increases beyond some threshold. Dialysate is removed from the cavity and there is no indication of how to replenish this quantity, which is a requirement in TPD. It is desirable to maintain the Dwell volume at the original Fill value and also supply fresh supply dialysate to compensate for the natural dilution by the UF and in an extreme case, Dadson could prematurely empty the cavity. Failure to account and accommodate for these issues prevents Dadson from performing evidence-based Tidal exchange points.

SUMMARY OF THE INVENTION

It is at least an object of the invention to provide a method and apparatus whereby exchange parameters, (time, volume, formulation etc) for the Tidal or any of the Batch modalities are determined from data collected during a PD treatment in real time by on board sensors. It is a further objective to provide a method and apparatus whereby a component of the data is the actual pressure changes due solely to UF generation. The pressure rise in the cavity can be separated into pressure due to UF and pressure due to patient movement. It is a further purpose of this invention to show that the sleep quality of the patient can be inferred from these pressure data. For example, if the breathing of the patient becomes compromised or changes dramatically. It is the further purpose of this invention to show that the heart rate of the patient can be extracted from collected pressure data. It is a further purpose of this invention to disclose a Fill Dwell and Drain methodology and apparatus that is used for evidence based determination of Tidal exchange points. It is the further purpose of this invention to disclosed methods and apparatus such that the traditional Batch process (Fill, Dwell and Drain) can be combined with the Tidal modality to produce a hybrid modality system according to the invention.

According to one aspect of the invention, there is provided a system of measuring a volume of a patient cavity for peritoneal dialysis (PD). The system comprises a cassette having a heated region and a sensor region. The sensor region measures pressure measurements. The system also comprises a volumetric pump supplying a fluid from one or more bags to the cassette or extracting the fluid from the cassette. A patient connection is in fluid communication with the cassette by way of a valve manifold. A microprocessor communicates with the sensor region and controls the heated region, the valve manifold, and the volumetric pump. The microprocessor reads and executes instructions from a computer-readable memory. The instructions involve: activating the volumetric pump to deliver discrete increments of the fluid to the cassette; receiving the pressure measurements from the sensor region; filtering rapid fluctuations in the pressure measurements to determine an accumulated pressure in the patient cavity; and correlating the accumulated pressure to the volume of the fluid in the patient cavity. The instructions may also measure the accumulated pressure and determine a volume of the patient cavity that induces physical discomfort. The instructions may also correlate the determination of the volume of the patient cavity to a full cavity condition. The instructions may also isolate pressure changes due to an ultrafiltrate (UF) volume increase from the accumulated pressure.

In another aspect of the invention, the instructions may determine a Tidal exchange point based on the isolated pressure changes. The accumulated pressure in the patient cavity may be monitored until it reaches a minimum cycle pressure, then the volumetric pump may be activated to deliver discrete increments of the fluid to the cassette until the patient cavity again reaches the full cavity condition.

In yet another aspect of the invention, the instructions may initiate a Drain phase based on the isolated pressure changes. The volumetric pump may reverse to reduce the accumulated pressure in the patient cavity until an empty condition occurs.

According to yet another aspect of the invention, there is provided instructions to isolate and/or record pressure changes due to a respiratory rate; heart rate; or determine sleep characteristics. There may also be instructions to determine transport kinetics based on at least one characteristic of the UF volume increase.

According to another aspect of the invention, there is provided a computer-implemented method of measuring a volume of a patient cavity for peritoneal dialysis (PD). The steps may comprise activating a volumetric pump to deliver discrete increments of a fluid from at least one bag to a cassette or extracting discrete increments of the fluid from the cassette; the cassette in fluid communication with the patient cavity by way of a valve manifold; measuring pressure measurements from a sensor region of the cassette; filtering rapid fluctuations in the pressure measurements to determine an accumulated pressure in the patient cavity; and correlating the accumulated pressure to the volume of the fluid in the patient cavity. The method may also comprise steps of measuring the accumulated pressure and determining a volume of the patient cavity that induces physical stress that causes discomfort. The determination of physical stress may be correlated to a full cavity condition.

According to yet another aspect of the invention, the computer-implemented method may comprise at least one of the steps of: isolating pressure changes due to ultrafiltrate (UF) volume increase from the accumulated pressure; determining a Tidal exchange point based on the isolated pressure changes; reversing the volumetric pump to reduce the accumulated pressure in the patient cavity; and monitoring the accumulated pressure in the patient cavity until it reaches a minimum cycle pressure; and activating the volumetric pump to deliver discrete increments of the fluid to the cassette until the patient cavity again reaches the full cavity condition.

According to other aspects of the invention, there is provided a computer-implemented method that comprises the steps of initiating a Drain phase based on the isolated pressure changes. The Drain phase may comprise reversing the volumetric pump to reduce the accumulated pressure in the patient cavity and reducing the accumulated pressure in the patient cavity until an empty condition occurs.

According to any aspect of the invention, the valve manifold may have a plurality of ports each coupled to a different bag from the at least one bag, each bag having a different solution. The instructions may dynamically adjust a formulation provided to the patient cavity from the different bags.

According to any aspect of the invention, the sensor region may measure optical properties. The microprocessor may execute instructions to: receive at least one optical property to detect air in the sensor region; and stop the volumetric pump in response to the detected air.

According to any aspect of the invention, the sensor region may measure temperature. The microprocessor may execute instructions to: receive the temperature associated with the sensor region and increase or decrease energy to the heated region to maintain a physiological temperature in the sensor region.

While several objectives have been identified above, the invention is not considered limited to any one or any combination of the objectives in particular. Rather, any system meeting at least one of the aforementioned objectives is considered within the scope of the present invention.

BRIEF DESCRIPTION OF THE DRAWINGS

An embodiment will now be described, by way of example only, with reference to the attached Figures, wherein:

FIGS. 1A to 1C shows perspective view with detailed views of a dialysis system;

FIG. 4A shows a screen shot of input data, having slow but increasing voltage level with a randomly variable fast voltage component superimposed, into the filtering capabilities algorithm according to a second example;

FIG. 4B shows a screen shot of the extracted slow component after the application of the filtering capabilities algorithm according to the second example;

DETAILED DESCRIPTION OF THE EMBODIMENT

Figure 1D:
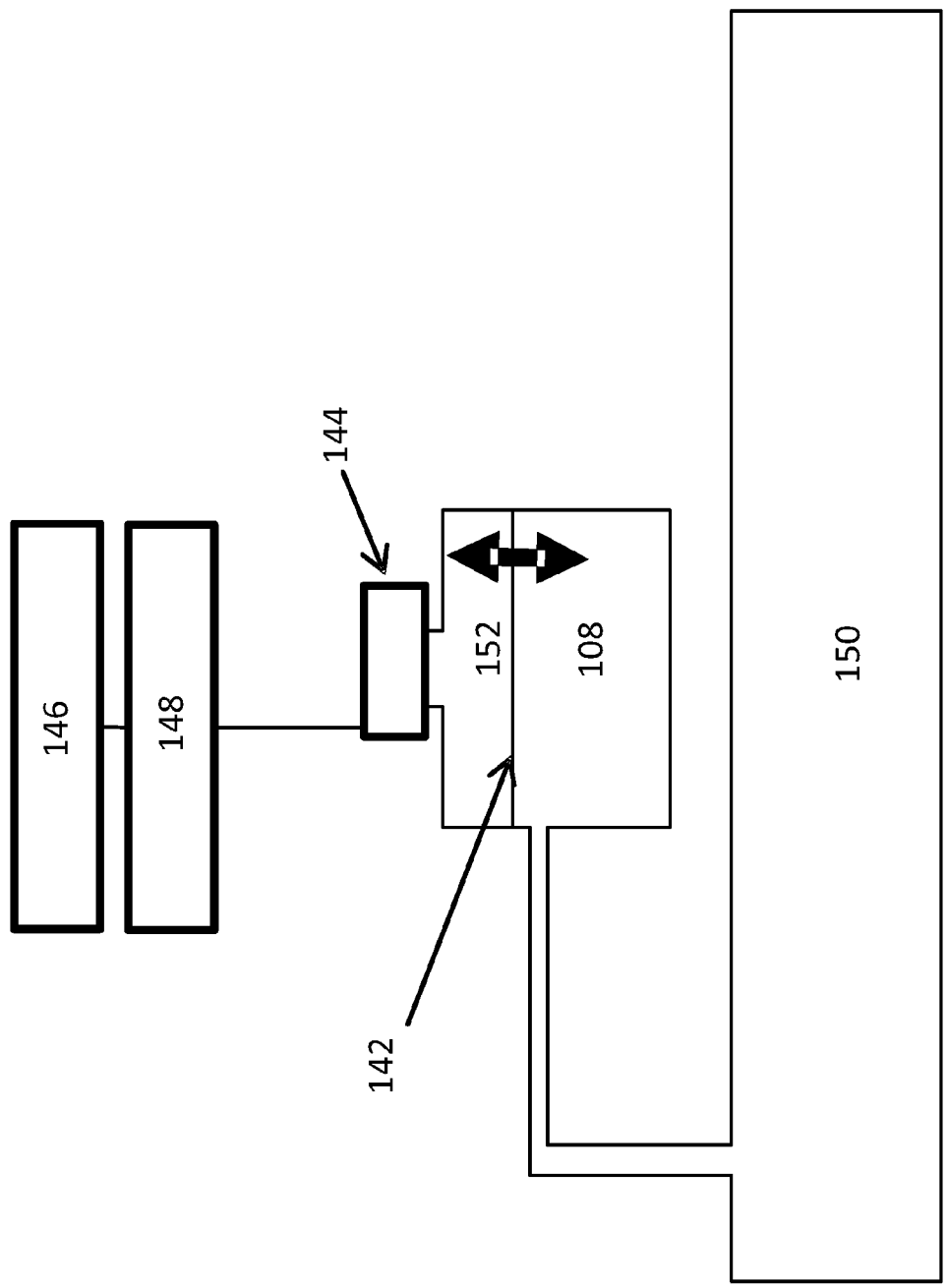
FIG. 1D shows a schematic view of the force sensor and associated electronics.

While the Background of Invention described above has identified particular problems known in the prior art, the present invention provides, in part, a new and useful application for peritoneal dialysis.

The basic element of the tidal modality has the following components as described herein. The system must fill the cavity with a prescribed volume of sterile fluid while ensuring that the entire fluid path remains sterile at all times. A fixed portion of that Fill volume is periodically drained and discharged as waste after a prescribed time interval. This time interval is known as the Dwell period and the periodic volumes drained during this prescribed time interval is referred to as the exchange volume. The exchange volume is then replaced with a volume less than that which was drained. The difference being what was estimated to be the Ultra Filtrate (UF) generated during the Dwell period. After a set number of Dwell periods the complete contents of the cavity is then drained. These basic elements to generally perform this tidal modality are described below.

The elements of the multiple modality system 100 are illustrated in FIGS. 1A to 1C, where a cycler 102 receives a cassette 104 (for example, as disclosed in CA 2,574,537 A1 and WO 2008/086619 A1). Fluid path sterility is ensured by the cassette. The cassette 104 comprises a heated region 106 and a diagnostic sensor region 108. This fluid-filled sensor region 108 mimics the chemical, physical, and biological properties of the fluid in the peritoneum 150.

A number of features ensures a sterile environment such as, for example, the system confirms that the cassette 104 is pressure and vacuum tight at the onset of the treatment. The system 100 confirms that fluid is flowing freely in the cassette 104 from bags 706 necessary for the prescribed formulation. The system 100 detects if any of the fluid lines (112, 114, 116) have unintended flow impediments. Furthermore, air is removed from cassette and any sterilization residue is removed as the system 100 performs Flush before Fill on all lines 112, 114, and/or 116. The system 100 performs a final confirmation that all fluid paths, in particular 114, contain only sterile fluid and has no air. The design and operating principle of this system 100 ensures that no air remains in the patient line 114 prior to the first Fill. The fluid pathways are designed such that all fluid movement passes, either to or from the pump 110, over the optical sensor region 124, which is encased by a transmitter-receiver diode pair or other form of optical detector. The presence of air instead of liquid in this region 124 defocuses and reduces the light intensity traversing this region 124 resulting in detection of any air in the system by the optical detector. If air is detected in any fluid path, then that fluid path is immediately blocked and the fluid in that path is discarded.

A volumetric pump 110 supplies pressure or vacuum to the cassette 104 and in this embodiment comprises a piston and cylinder configuration attached to the cassette 104. Solution is provided to the cassette 104 by way of solution connections 112 and pump 110. A patient connection 114 is connected to the patient in conjunction with a drain 116 by way of a valve manifold 126 having a plurality of ports P1 to P6. FIG. 1C shows a schematic of the sensor region 108 of a single-use cassette 104 used by the cycler 102. The fluid in this region 108 emulates the properties of the fluid in the peritoneum 150. Therefore, measurements taken within this region 108 are indicative of the properties of the fluid in the peritoneum 150. The sensor region 108 measures pressure 120, temperature 122, and optical properties 124, but others such as chemical sensors (not shown) could be incorporated.

For the Fill process, the cavity is completely filled with the volume of dialysate that was prescribed by the clinician and at a rate that does not discomfort the patient. This fluid should be provided at the prescribed physiological temperature. In addition, it is preferable that the formulation of this fluid is adjustable at any given exchange point and every effort should be made not to generate by-products by overheating the fluid. Pump 110 draws a prescribed volume of fluid from each of the bags connected to 112 in a programmed sequence to generate a fully formulated biocompatible formulation within the body of the pump 110. The fluid is prepared and delivered in discrete (0-50 mL) increments. Therefore, each increment can be a unique mixture of the solution bags that are attached to ports hence the delivered formulation can be changed at any exchanged point.

This fluid is then delivered to the patient's cavity by running the pump 110 in reverse. The reverse fluid path is such that the fluid must pass over the heated region 106 by way of port P7 and P8 before it reaches the patient's cavity. In addition, the fluid pathways are designed such that all fluid movement must at some point, either to or from the pump 110, must pass by the optical sensor region 124 which is encased by a transmitter-receiver diode pair. The presence of air instead of liquid in this region 124 defocuses and hence reduces the light intensity traversing this region 124 resulting easy detection of any air in the system. If air is detected in any the fluid path that fluid path is immediately blocked and that fluid is discarded. The valve manifold is computer controlled such that only the required port(s) and fluid paths are in communication with the pump for the required filling action. For example, during the filling of the cavity the pump 110 communicates with the cavity via ports P7, P8, and P5. All other ports are isolated from the pump 110.

The Dwell period represents the most effective portion of the treatment for waste removal. During this time, the majority of the waste is transferred from the blood to the dialysate. Therefore, for optimum performance it is preferable to have an objective manner to determine when this phase is no longer optimal. Prior methods and systems use a fixed time for this purpose. The fixed time is not an effective monitor since predetermination of the exact metabolic rate of the patient in advance of the treatment is not possible and therefore a fix dwell period time is inappropriate. The embodiment described herein provides an evidence-based method to determine when the Dwell is completed.

During Drain, the largest safety limitations in all PD systems that currently promotes the tidal modality is their inability to determine if the cavity is truly empty at the Final Drain. Since all such systems rely on the difference in Fill volume and Drain volume to determine UF, any error in the Final Drain volume generates an error in the UF calculation. In addition, it is not uncommon for such systems to recommend an additional Last Fill after the end of the tidal modality. If the cavity has not been fully drained at the end of the tidal modality, there exists the danger that this Last Fill will induce severe discomfort to the patient due to overfilling of the cavity.

In the present embodiment, the pump 110 is used to drain the cavity using port P5 and P6 in sequence. Port P7 is isolated from the pump 110 by a one-way valve that only allows fluid to pass from the pump 110 to the heated region 106 and never back from the heated region 106 to the pump 110. Therefore, this one-way valve retains sterility of the fluid path by prohibiting fluid leaving the cavity to re-enter the heated region 106. Once the pump 110 has withdrawn a discrete volume from the cavity via port P5, port P5 is then closed and port P6 opened. Pump 110 is reversed and the pump 110 is emptied. The method involves pressure monitoring to detect when the cavity is empty and the method is independent of Drain speed. Moreover, the Drain speed is optimized independently of the Fill speed. The system 100 also recognizes kinks and blockages in lines and distinguishes between air and liquid leaving cavity. The system 100 can be positioned such that a gravity drain is permissible in the event of a pump failure. The drain algorithm differentiates between an empty cavity and block drain line.

The present embodiment incorporates pressure monitoring as the objective parameter to improve Tidal modality as described above. The pressure sensor 120 measurements in combination with an appropriate algorithm permits the cycler 102 to: isolate pressure changes due only to UF; determine the volume of the cavity; determine when the cavity is full; determine the time when an exchange should be initiated; and determine when the cavity is empty. These additional features when working synergistically provide the outcomes which are required for evidence based tidal.

The pressure changes due to UF alone are isolated based on the system 100 being a closed liquid loop as can be seen in FIG. 1D, with rigid walls, except for the pressure sensor region 120, and has no or insignificant air pockets. That is the pressure changed seen in the pressure sensing region 120 is proportional to the volume increase provided the closed loop is full of liquid. Since a fluid is an incompressible medium, the result is dP/dV=constant. If V is increased, then P must also increase proportionally. Since the only moveable element is the silicone membrane 142 acting from the liquid sensor region 108 to an air filled area 152, the deformation of the membrane 142 is detected by a force on the force transducer 144 that is pressure and vacuum sealed. The force transducer 144 generates a voltage change that is converted from analog to digital and recorded by a microprocessor 148 into memory 146. This data is then digitally filtered by a filtering algorithm in memory 146 executed by the microprocessor 148. The filtering algorithm compares the slopes (dP/dt) of adjacent data points. The UF process is a slow process in comparison to other factors that may increase the cavity pressure. Therefore, if the slope at t+Δt is greater than a given percentage of the value at t, then the detected value at t is discarded as a non-UF pressure rise and an extrapolated value is calculated for t+Δt. This extrapolated value replaces the discarded value. This process is repeated throughout the Dwell period.

Figure 3A:
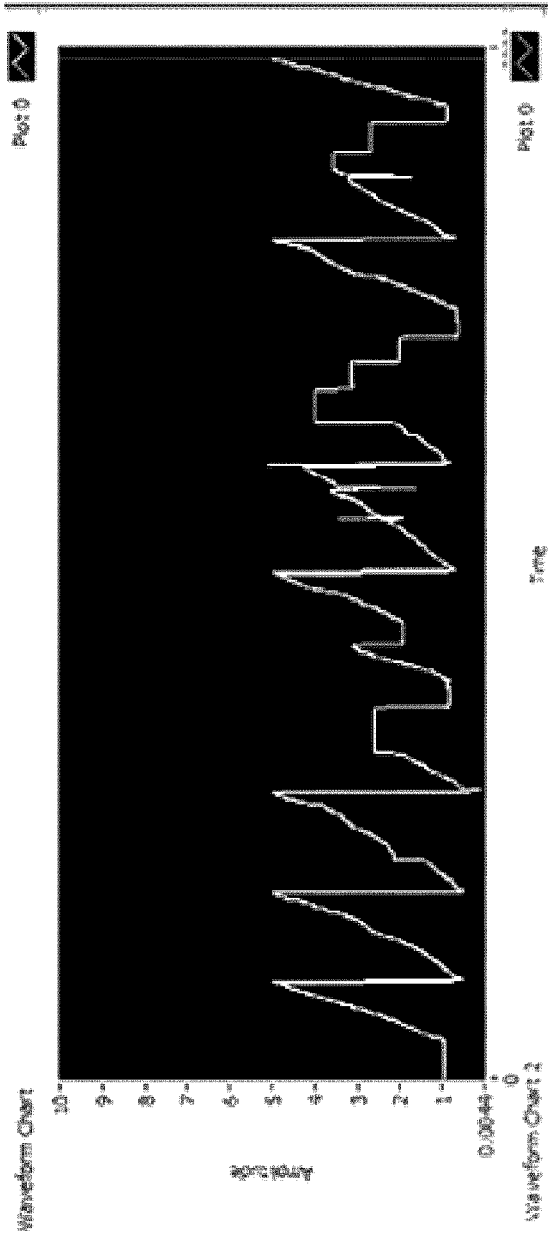
FIG. 3A shows a screen shot of input data, having slow but increasing voltage level with a randomly variable fast voltage component superimposed, into the filtering capabilities algorithm according to a first example.
Figure 3B:
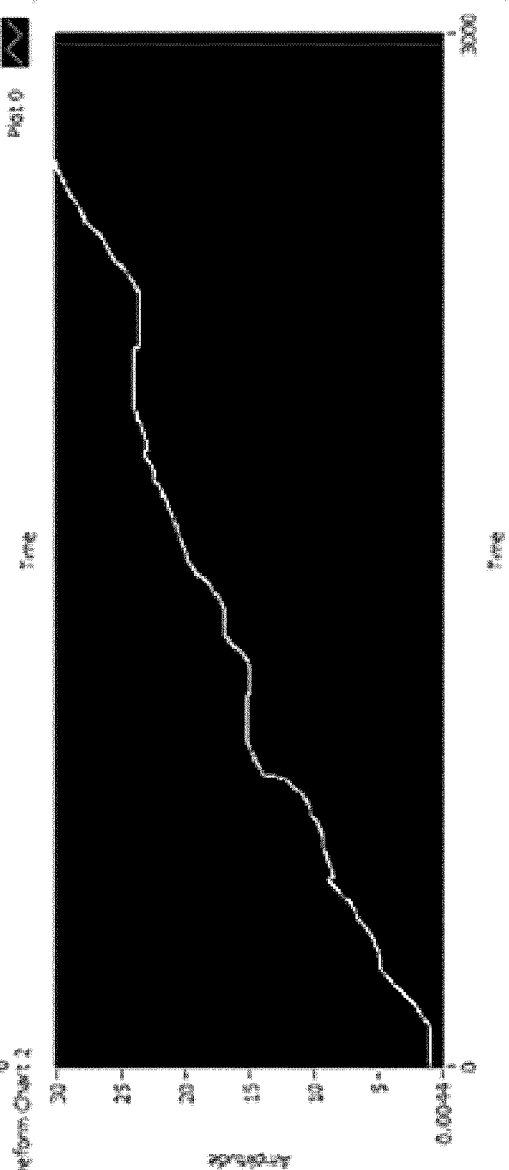
FIG. 3B shows a screen shot of the extracted slow component after the application of the filtering capabilities algorithm according to the first example.

Examples of how the algorithm can separate pressure changes due to ultrafiltration from other events than can cause the cavity pressure to rise as shown in FIGS. 3 and 4. The top curves shown in FIGS. 3A and 4A are simulated (enforced) pressure changes. The bottom curve shown in FIGS. 3B and 4B are processed by the algorithm and reported as pressure changes due to UF at the same time increment. This is possible because the timescales associated with pressure due to the enforced UF is long in comparison to pressure changes due to simulated patient movement or biological functions.

Figure 2:
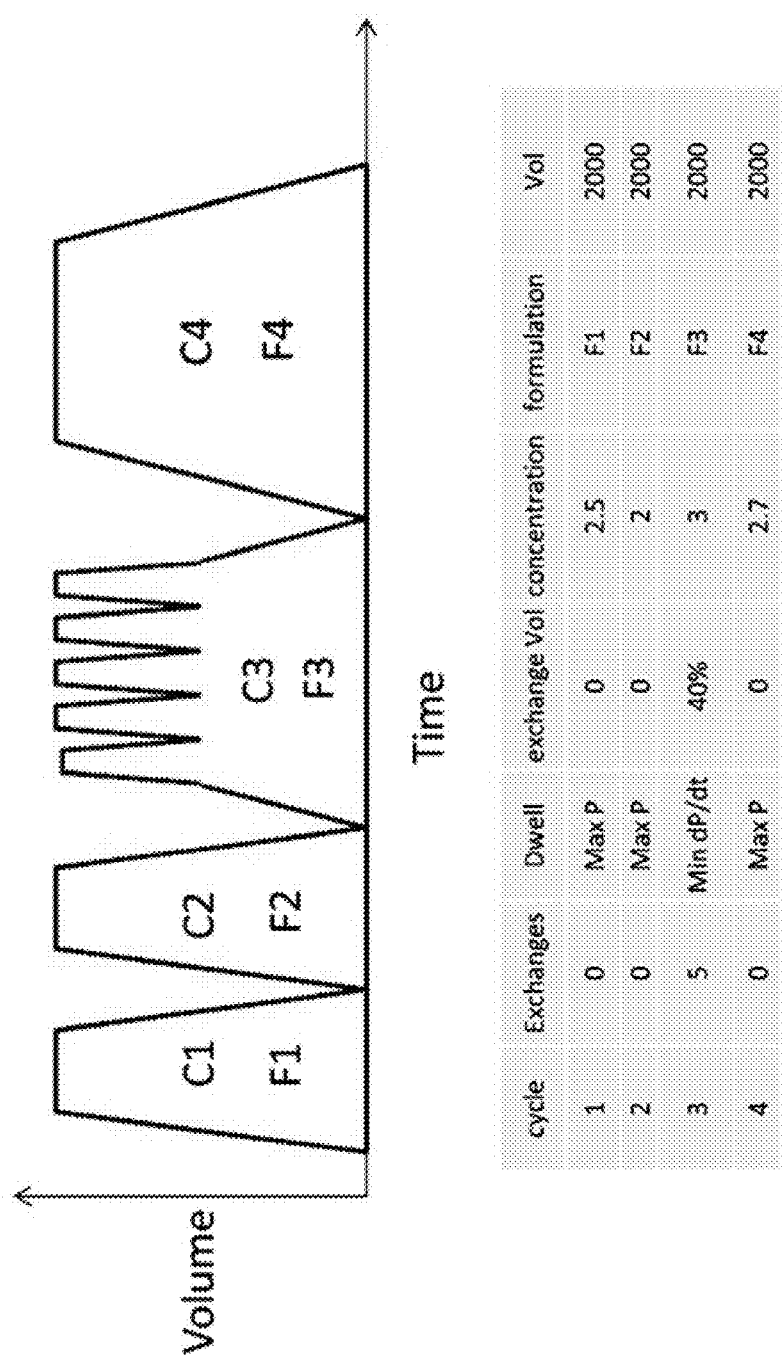
FIG. 2 shows a graph and table of a treatment and formulation for the dialysis system.

The ability to correlate pressure increase with UF volume increase during the Dwell provides the additional opportunity to track different size molecules with different transport kinetics and allowing the targeting of specific species with specific formulations, specific Dwell times, and specific exchange times. An example is shown in FIG. 2, where there is an implementation of specific formulation and dwell time for fast high mobility species (C1 and C2), followed by Tidal for intermediate C3, followed by C4 cycle for slow species.

The algorithm monitors pressure during the Dwell by either focusing on pressure increment or rate of change of pressure and differentiates between pressure change due to UF and other sporadic pressure changes. The pressure monitoring options comprise at least one of determining when Dwell is complete, reporting on Dwell efficiencies (d[UF]/dt), heart rate monitor, breathing rate, and/or sleep quality option. When reporting on Dwell efficiencies by monitoring and recording the rate of UF increase, characterization of membrane transport properties can be inferred.

Figure 5:
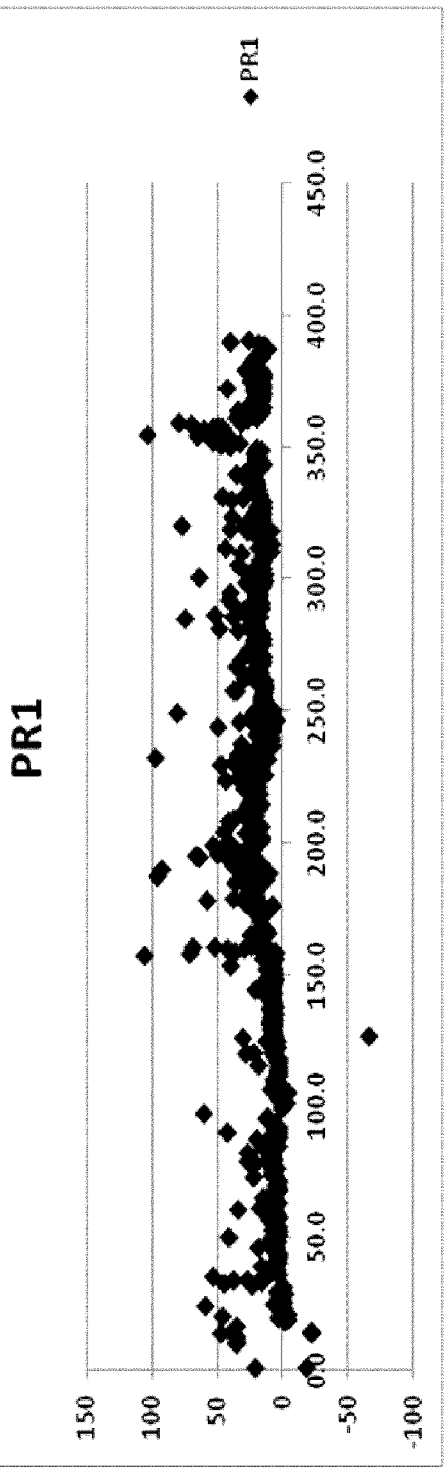
FIG. 5 shows an in-vivo pressure history collected by the on-board pressure sensors during a standard batch process on a patient using this cycler.

FIG. 5 shows the in-vivo pressure history collected by the on-board pressure sensors 120 during a standard batch process on a patient using this cycler 102. In this mode the cycler 102 performed as a standard cycle with the ability to monitor and collect data of the pressure in the peritoneal cavity at 30 sec intervals. In this example, the patient was awake during the treatment and was allowed natural movement, hence the large pressure spikes that were present in FIG. 5 coincided with this movement. If such a trace was observed during the night treatment, it would be indicative of the patient's sleep pattern. These large perturbations could be indicative of an underlying clinical issue. One such issue is that the patient's breathing may have been compromised. If the data sample rate was increased from 0.03 Hz to every 10 Hz, then the patient's natural breathing pattern and heart rate could be extracted from this data since both express themselves as distinctive and reproducible pressure perturbations superimposed on the natural UF pressure profile. This again provides useful clinical information.

Figure 6:
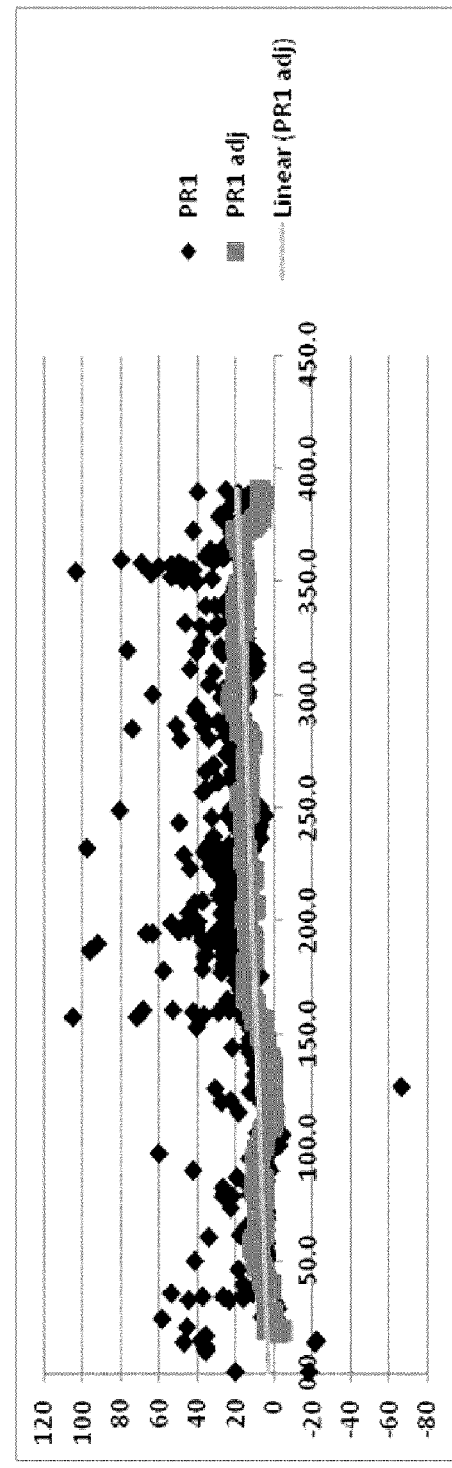
FIG. 6 demonstrates an effect of the dialysis system on FIG. 5 data.

Using the data from FIG. 5, FIG. 6 demonstrates the effect of incorporating the Dwell algorithm as described above (PR1). The new data generated is shown in grey with a trendline shown in light grey. Note the average pressure increase in FIG. 5 is the same as in FIG. 6 but the perturbations due to non-UF pressure changes, such as patient movement has been removed by the Dwell algorithm. Thus, the cycler 102 may record the pressure changes in the peritoneum 150 that were due only to UF.

Figure 7:
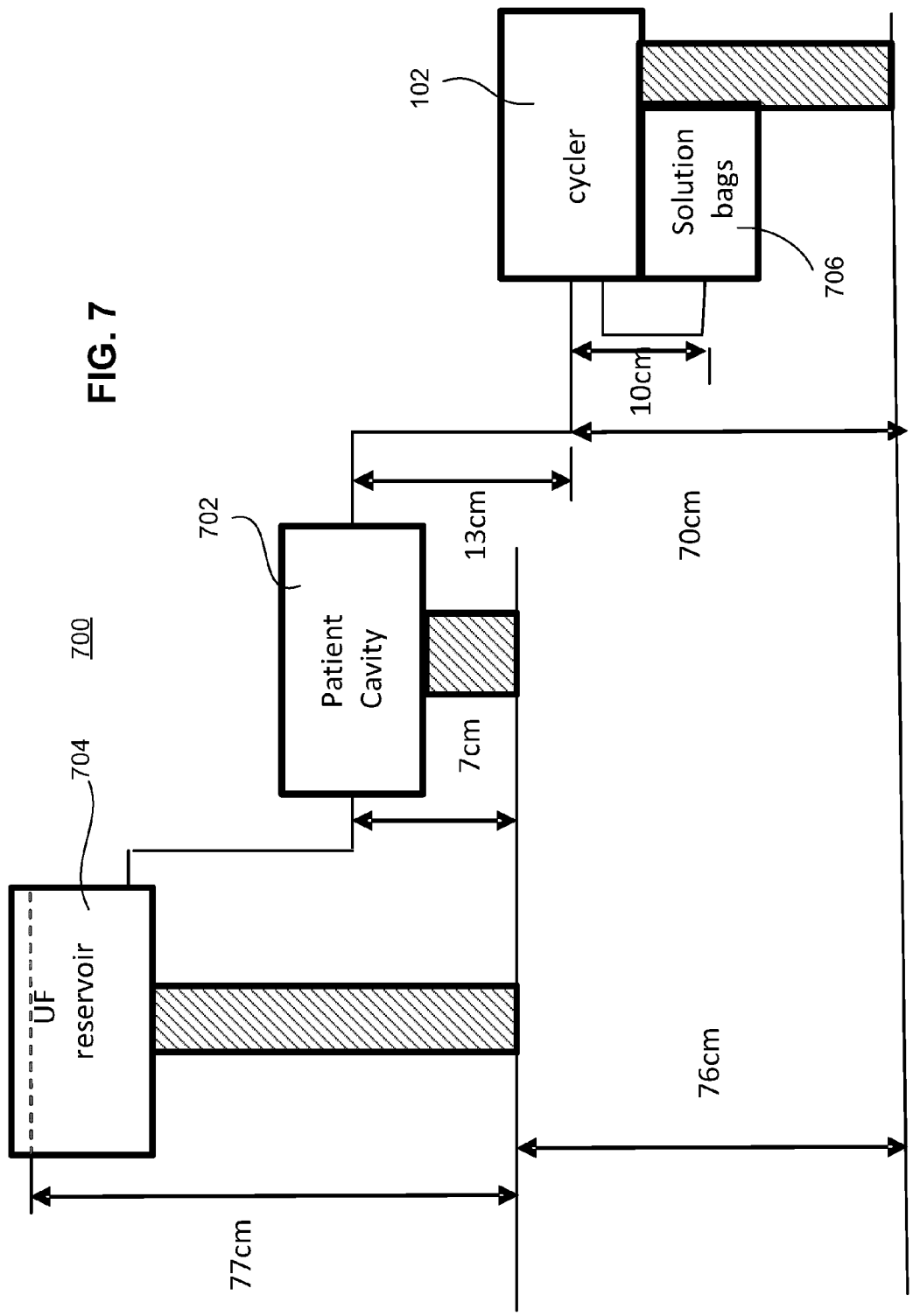
FIG. 7 shows a schematic of a characterization apparatus used to demonstrate the properties of a constructed cycler.

FIG. 7 shows the apparatus used to demonstrate how the cycler 102 can be used to measure the cavity volume. For this initial design, due to safety considerations the "patient cavity" 702 used in FIG. 7 was a simulated. The simulated patient cavity 702 is constructed to mimic the performance of a real peritoneal cavity. The cavity 702 comprises an inner flexible skin bonded by a rigid frame and has the ability to trap air pockets within the inner flexible skin. This rigid frame is surrounded by a heater blanket such that the temperature at the interior of the inner skin is kept at body temperature. Two inputs tubes were inserted into the cavity 702. The first input tube was terminated by a peritoneal catheter and was inserted into the center of the cavity 702. The second input tube was used as a means to add extra fluid from an independent source (UF reservoir) placed above the patient cavity 702, thus simulating a controlled UF inflow once the appropriate valve was opened.

Figure 8:
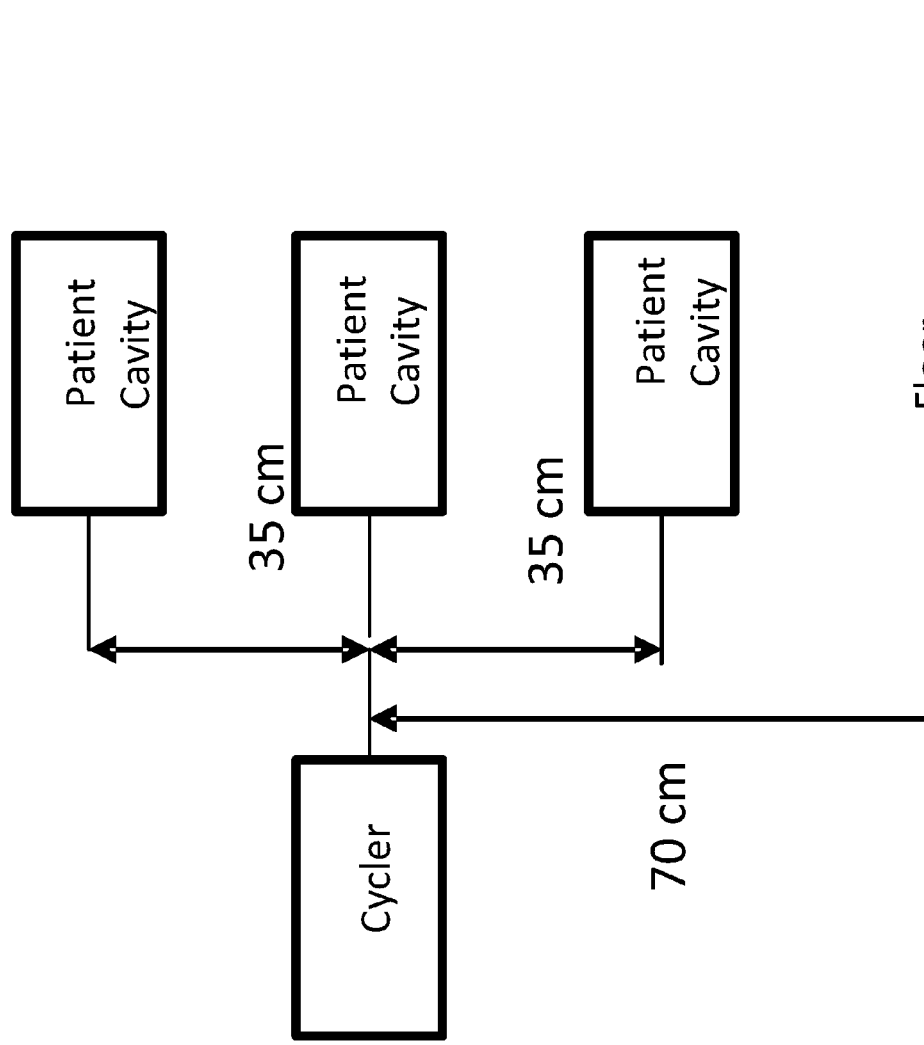
FIG. 8 shows a schematic of locations of a patient cavity height relative to the cycler.
Figure 9:
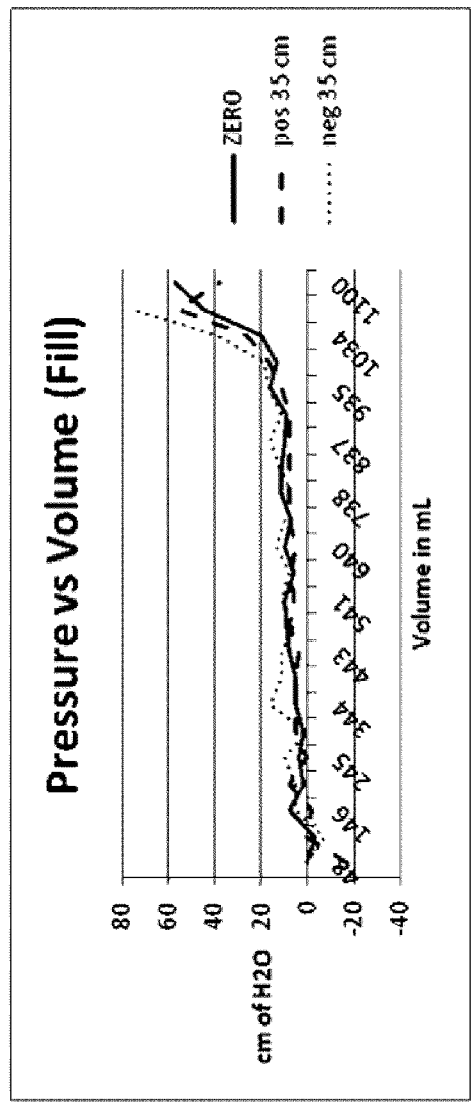
FIG. 9 shows a plot of pressure recorded in the pressure sensing region when the cavity is being filled.
Figure 10:
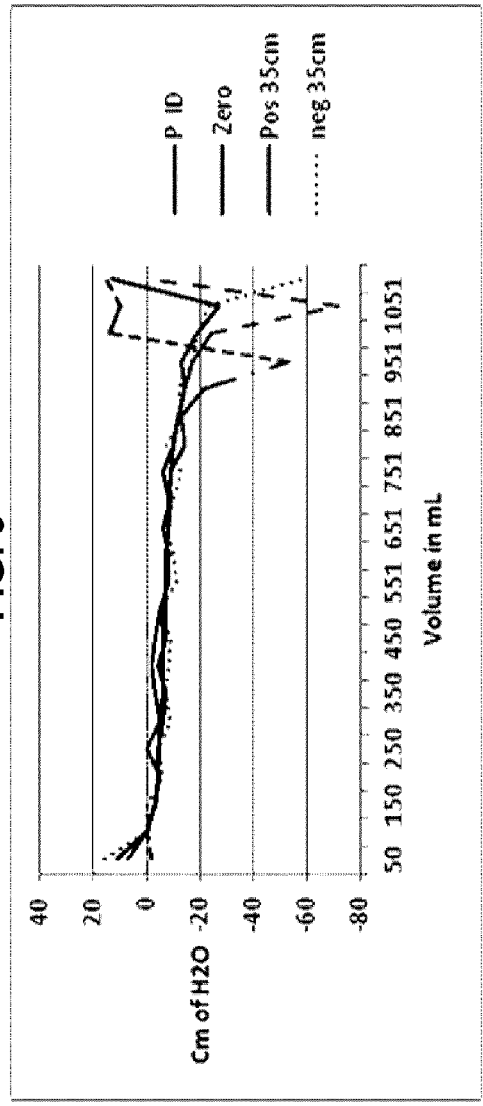
FIG. 10 shows a plot of pressure recorded in the pressure sensing region when the cavity is being emptied.

FIG. 8 shows the three locations of the patient cavity 702 height relative to that of the cycler 102. The maximum upper and lower ranges were +/−100 cm. This was the pre-set value of the syringe pump that powered the fluid movement. This value could be increased to +/−200 cm if required. Fluid was admitted to the cavity 702 in each of the three peritoneal cavity positions (−35 cm, 0 cm, and +35 cm) and the pressure recorded in the pressure sensing region 120 was recorded as shown in FIG. 9. The inflection point where the inner flexible skin is now being stressed occurs at a similar volume in each case. This stressing of the cavity 702 indicates that the cavity 702 is full. This admitted volume is then the volume of the cavity. This determines that the stressing of the cavity 702 indicates the fill volume of the cavity 702. The inverse to FIG. 9 is achieved when the cavity 702 is empty as shown in FIG. 10. That is the peritoneum 150 is stressed as a result of an empty cavity 702. Again the stress point is generally independent of the height difference between the cycler 102 and the cavity 702. The system incorporates a number of algorithms that once a stress point (inflection) is detected, the microprocessor 148 executing the algorithm examines the inflection to determine if it was caused by a flow impediment in the line. For example, if the inflection was caused by a kind in the line, a flow reversal would generate the inverse inflection. If the inflection was caused by an empty cavity, not inflection would be generated.

Figure 11:
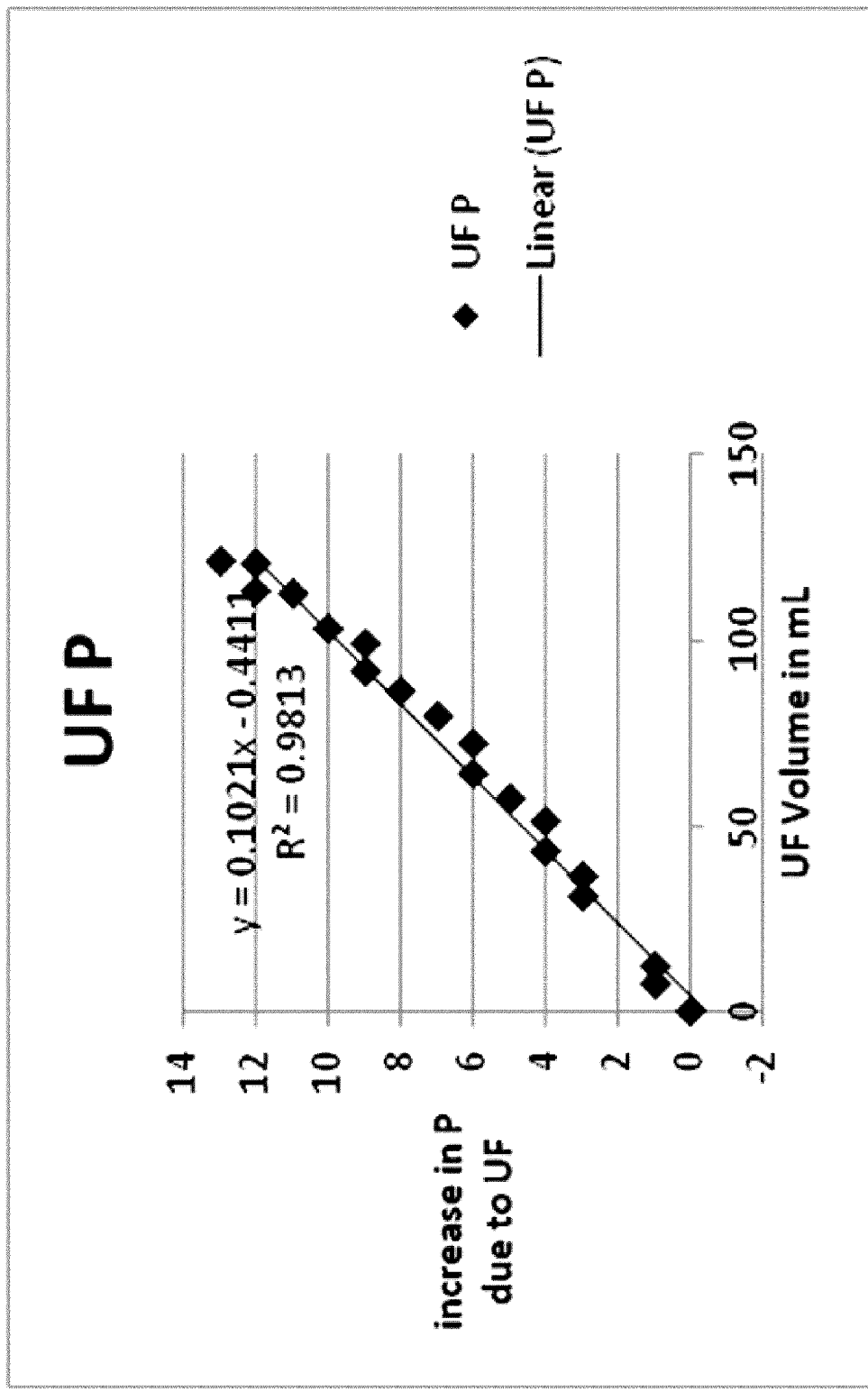
FIG. 11 shows a plot demonstrating that the change in pressure versus volume is constant.

The UF volume be tracked by monitoring the induced pressure increment. This concept is based on a closed loop fluid path dP/dV being constant. The apparatus 700 shown in FIG. 7 was used. The UF volume was recorded at 1 min time intervals by noting the increase in weight of the cavity 702 which was positioned on a scale. Concurrently to this, the pressure increased in the sensor region of the cycler 102 was recorded. FIG. 11 shows that dP/dV was a constant with an $R^2$ of 0.9813. Therefore dV/dt=k·dP/dt, where k is constant, and dV/dt and dP/dt are the change in volume and pressure over time. Given this, by monitoring the change in pressure over time, the pressure increment with time is proportional to the UF volume increment with time. Hence, the UF volume generated during the Dwell may be objectively measured by monitoring the corresponding pressure increase.

Figure 12:
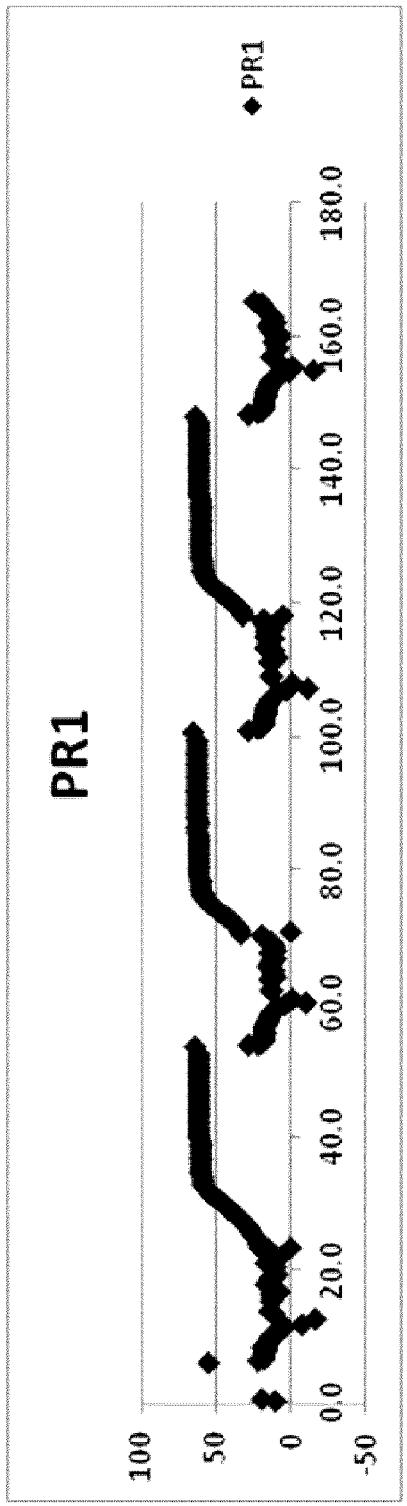
FIG. 12 shows a plot of pressure versus time for three consecutive cycles of a batch process.
Figure 13:
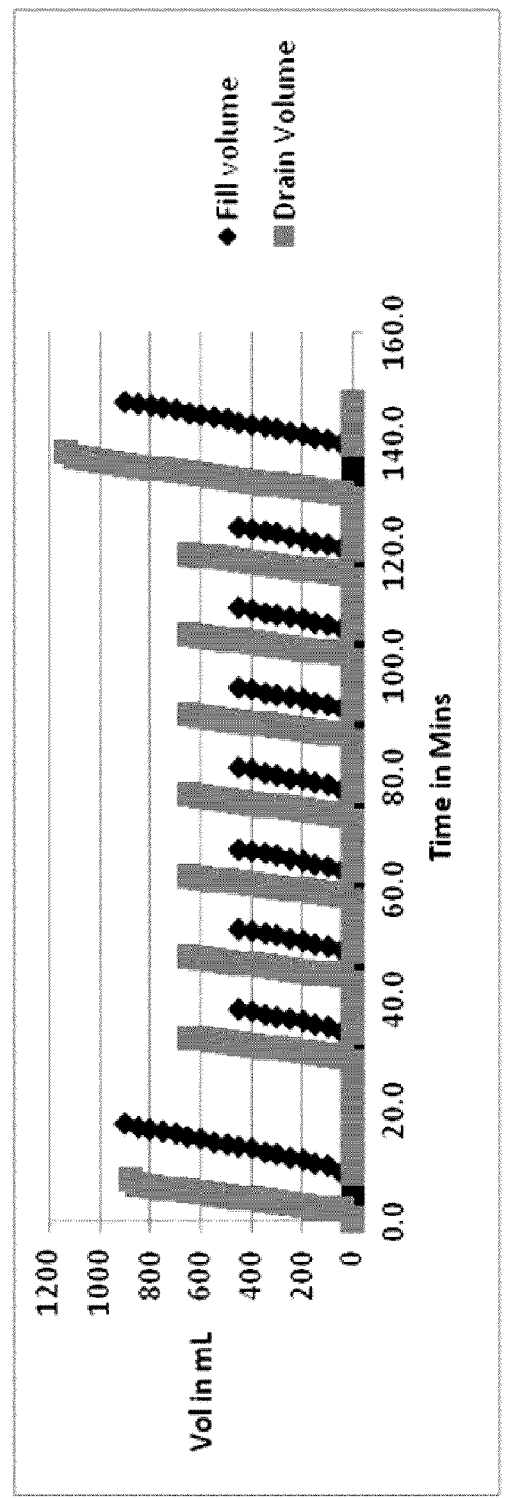
FIG. 13 shows a plot of the measured fill and rain volume versus time a typical tidal process.

The cycler 102 may determine the optimum time in which to terminate the Dwell by monitoring the value of dP/dt. When dP/dt becomes zero, the forward direction of UF is terminated. At this point the Dwell is terminated thus avoiding UF flow reversal. This is shown in FIG. 12 where a plot of pressure versus time of three consecutive cycles of a typical batch process is shown. The graph shows the point at which dP/dt=0 for each cycle where this signals the effective ends of the Dwell for each cycle. There is no significant clinical benefit for prolonging the Dwell beyond these periods without creating the conditions for UF reversal. The entire UF profile is captured for each cycle. Measuring the entire UF profile for each cycle allows for the direct extraction of the transport rates and the evolution time of each component used in the 3-pore model. Thus individual transport kinetics for each treatment cycle are determined.

Figure 14:
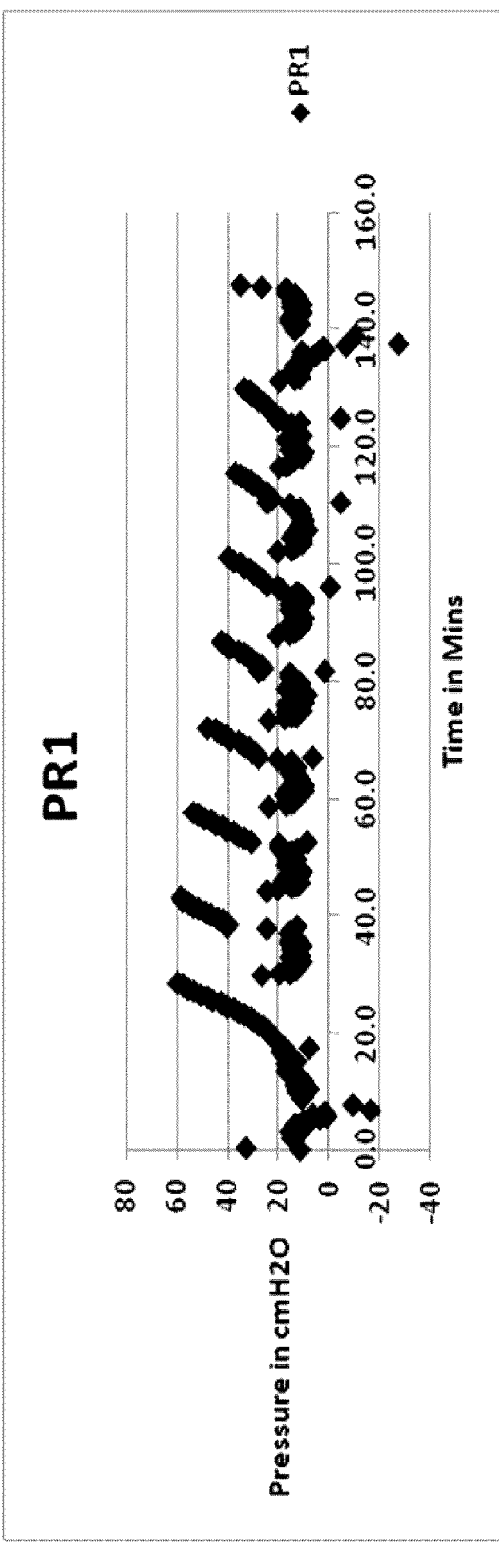
FIG. 14 show a plot of the pressure versus time for the tidal process.

The same experiment was repeated using standard Tidal modality with the measured Fill and Drain volumes generated during the treatment shown in FIG. 14. The prescription was an initial Drain, a Fill followed by 7 exchanges, a full drain and then a final Fill. The volume of the first fill and the last fill were selected to be the same.

The exchange drain volumes and the corresponding fill volume were the same for each exchange as per the prescription requirements. However, because the total UF per exchange is deliberately underestimated and hence creating the conditions for over fill at the last Fill, the system 100 was agile enough to continuing the drain process until the cavity was empty prior to the Last fill thus avoiding over fill condition, a serious safety issue.

Concurrent to the volume measurements the UF being admitted into the cavity at was monitored by tracking dP/dt. The UF flow rate was designed to decrease with time as would be expected under typical treatment conditions. FIG. 14 shows the measure pressure increase with time. The slope of the Pressure vs time curve decreased in line with the UF rate reduction.

Therefore, two quantitative methods determine when to stop the dwell and initiate an evidence based exchange. The system 100 may be programmed to perform the exchange if dP/dt=zero (as shown in FIG. 12) or drops below a certain threshold value (FIG. 14).

Figure 15:
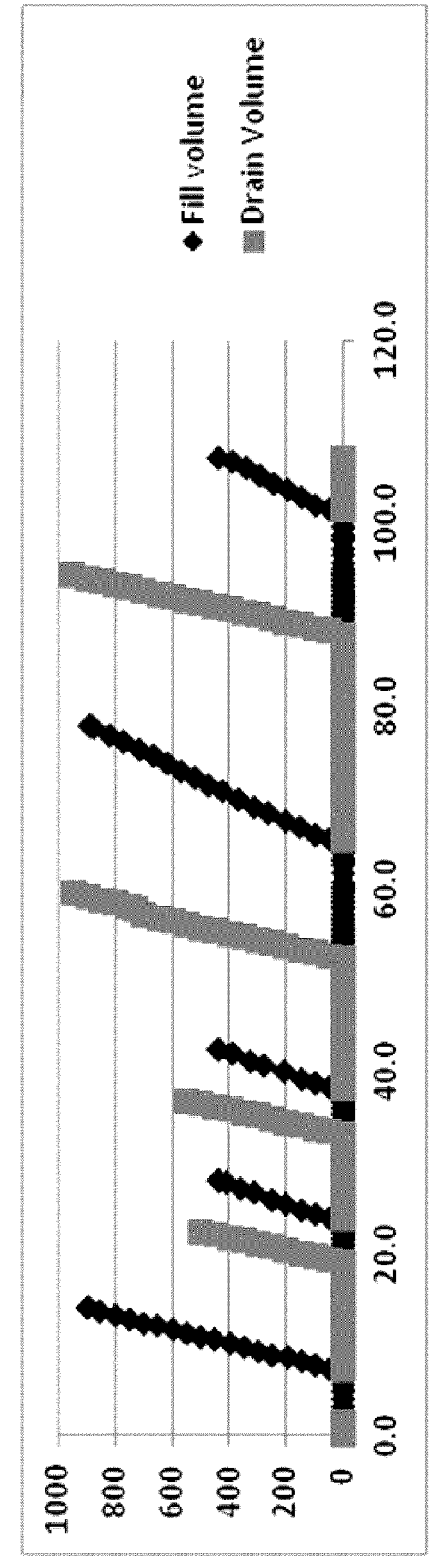
FIG. 15 shows a plot of the Fill and Drain volumes of a treatment that combines Tidal and batch processes.

The Tidal and Batch process as described herein are combined. Since the cycler 102, as previously described, is able to determine when to terminate the Dwell, is fully volumetric, can measure the cavity volume, can determine when the cavity is full or empty and can vary the formulation at each cycle or exchange point, the traditional batch process may be blended with the tidal modality. An example of the Fill, Dwell, and Drain times are shown in FIG. 15 along with the concentration table for each Cycle/exchange. The initial state of the patient is "dry". The cycler 102 performs one Fill followed by two tidal exchanges. After the second exchanged the batch process was implemented, complete drain and refill with fresh dialysate. The treatment was concluded with a partial fill that constitute a "wet Phase.

TABLE 1

Prescription table

| N | % Conc | Fill mL |
|---|--------|---------|
| 1 | 2.27 | 0.9 |
| 2 | 2.51 | 0.45 |
| 3 | 2.75 | 0.45 |
| 4 | 2.99 | 0.9 |
| 5 | 3.23 | 0.45 |

The measurements that are described herein may not simply be measured, but may also be monitored, tracked, recorded to memory, extracted by way of a USB port 180, streamed over a network to other computer systems at local or remote locations, or discarded.

The above-described embodiments are intended to be examples of the present invention and alterations and modifications may be effected thereto, by those of skill in the art, without departing from the scope of the invention, which is defined solely by the claims appended hereto.

What is claimed is:

1. A peritoneal dialysis (PD) system comprising:
   a cassette comprising a heated region and a sensor region, the sensor region measuring pressure measurements;
   a volumetric pump supplying a fluid from at least one bag to the cassette or extracting the fluid from the cassette;
   a patient connection in fluid communication with the cassette by way of a valve manifold;
   a microprocessor communicating with the sensor region and controlling the heated region, the valve manifold, and the volumetric pump;
   a computer-readable memory, the microprocessor reading and executing instructions from the computer-readable memory to configure the microprocessor to:
      activate the volumetric pump to deliver discrete increments of the fluid to the cassette;
      receive the pressure measurements from the sensor region;
      filter rapid fluctuations in the pressure measurements to determine an accumulated pressure in the patient cavity; and
      correlate the accumulated pressure to a volume of the fluid in the patient cavity.

2. The system according to claim 1, the computer-readable memory further comprising instructions to configure the microprocessor to: measure the accumulated pressure and determine the volume of fluid in the patient cavity that induces physical stress.

3. The system according to claim 1, the computer-readable memory further comprising instructions to configure the microprocessor to: correlate the determination of the volume of fluid in the patient cavity to a full cavity condition.

4. The system according to claim 3, the computer-readable memory further comprising instructions to configure the microprocessor to: isolate pressure changes due to ultrafiltrate (UF) volume increase from the accumulated pressure.

5. The system according to claim 4, the computer-readable memory further comprising instructions to configure the microprocessor to: determine a Tidal exchange point based on the isolated pressure changes.

6. The system according to claim 5, the computer-readable memory further comprising instructions to configure the microprocessor to: reverse the volumetric pump to reduce the accumulated pressure in the patient cavity.

7. The system according to claim 6, the computer-readable memory further comprising instructions to configure the microprocessor to: monitor the accumulated pressure in the patient cavity until it reaches a minimum cycle pressure; and at the minimum cycle pressure, activate the volumetric pump to deliver discrete increments of the fluid to the cassette until the patient cavity again reaches the full cavity condition.

8. The system according to claim 4, the computer-readable memory further comprising instructions to configure the microprocessor to: initiate a Drain phase based on the isolated pressure changes.

9. The system according to claim 8, the computer-readable memory further comprising instructions to configure the microprocessor to: reverse the volumetric pump to reduce the accumulated pressure in the patient cavity.

10. The system according to claim 9, the computer-readable memory further comprising instructions to configure the microprocessor to: reduce the accumulated pressure in the patient cavity until an empty condition occurs.

11. The system according to claim 4, the computer-readable memory further comprising instructions to configure the microprocessor to: determine transport kinetics based on at least one characteristic of the UF volume increase.

12. The system according to claim 3, the computer-readable memory further comprising instructions to configure the microprocessor to: isolate pressure changes due to a respiratory rate.

13. The system according to claim 3, the computer-readable memory further comprising instructions to configure the microprocessor to: isolate pressure changes due to a heart rate.

14. The system according to claim 1, further comprising: the sensor region measuring optical properties; and the computer-readable memory further comprising instructions to configure the microprocessor to: receive at least one optical property to detect air in the sensor region; and stop the volumetric pump in response to the detected air.

15. The system according to claim 1, wherein the valve manifold comprises a plurality of ports each coupled to a different bag from the at least one bag, each bag having a different solution; the computer-readable memory further comprising instructions to configure the microprocessor to: dynamically adjust a formulation provided to the patient cavity from the different bags.

16. The system according to claim 12, the computer-readable memory further comprising instructions to configure the microprocessor to: record at least one respiratory cycle.

17. The system according to claim 1, further comprising the sensor region measuring temperature; and the computer-readable memory further comprising instructions to configure the microprocessor to: receive the temperature associated with the sensor region and increase or decrease energy to the heated region to maintain a physiological temperature in the sensor region.

18. The system according to claim 1, the computer-readable memory further comprising instructions to configure the microprocessor to: determine sleep characteristics.

19. A computer-implemented method of performing diagnostic measurements during peritoneal dialysis (PD), comprising steps of:
    activating a volumetric pump to deliver discrete increments of a fluid from at least one bag to a cassette or extracting discrete increments of the fluid from the cassette; the cassette in fluid communication with the patient cavity by way of a valve manifold;
    measuring pressure measurements from a sensor region of the cassette;
    filtering rapid fluctuations in the pressure measurements to determine an accumulated pressure in the patient cavity; and
    correlating the accumulated pressure to a volume of the fluid in the patient cavity.

20. The computer-implemented method according to claim 19, further comprising steps of: measuring the accumulated pressure and determining the volume of fluid in the patient cavity that induces physical stress to cause discomfort.

21. The computer-implemented method according to claim 20, further comprising steps of: correlating the determination of the physical stress to a full cavity condition.

22. The computer-implemented method according to claim 21, further comprising steps of: isolating pressure changes due to ultrafiltrate (UF) volume increase from the accumulated pressure.

23. The computer-implemented method according to claim 22, further comprising the steps of: determining a Tidal exchange point based on the isolated pressure changes.

24. The computer-implemented method according to claim 23, further comprising steps of: reversing the volumetric pump to reduce the accumulated pressure in the patient cavity.

25. The computer-implemented method according to claim 24, further comprising steps of: monitoring the accumulated pressure in the patient cavity until it reaches a minimum cycle pressure; and activating the volumetric pump to deliver discrete increments of the fluid to the cassette until the patient cavity again reaches the full cavity condition.

26. The computer-implemented method according to claim 22, further comprising the steps of: initiating a Drain phase based on the isolated pressure changes.

27. The computer-implemented method according to claim 26, memory further comprising steps of: reversing the volumetric pump to reduce the accumulated pressure in the patient cavity.

28. The computer-implemented method according to claim 27, further comprising steps of: reducing the accumulated pressure in the patient cavity until an empty condition occurs.

29. The computer-implemented method according to claim 22, further comprising steps of: isolating pressure changes due to a respiratory rate.

30. The computer-implemented method according to claim 22, further comprising steps of: isolating pressure changes due to a heart rate.

31. The computer-implemented method according to claim 22, further comprising steps of: determining transport kinetics based on at least one characteristic of the UF volume increase.

32. The computer-implemented method according to claim 19, further comprising the steps of: dynamically adjusting a plurality of ports of the valve manifold, each of the ports coupled to a different bag from the at least one bag, each bag having a different solution, to modify a formulation provided to the patient cavity from the bags.

33. The computer-implemented method according to claim 19, further comprising steps of: measuring at least one optical property from the sensor region to detect air in the sensor region and stop the volumetric pump in response.

34. The computer-implemented method according to claim 19, further comprising steps of: measuring a temperature associated with the sensor region; and increasing or decreasing energy to the heated region to maintain a physiological temperature within the sensor region.

35. The computer-implemented method according to claim 19, further comprising steps of: measuring sleep characteristics.

\* \* \* \* \*